United States Patent [19]

Fogarty et al.

[11] Patent Number: 4,860,769
[45] Date of Patent: Aug. 29, 1989

[54] IMPLANTABLE DEFIBRILLATION ELECTRODE

[75] Inventors: Thomas J. Fogarty, 770 Welch Rd., Palo Alto, Calif. 94304; Albert K. Chin, Palo Alto; Joe Feehan, Cupertino, both of Calif.

[73] Assignees: Thomas J. Fogarty; Ventritex, Inc., Santa Clara County, Calif.

[21] Appl. No.: 120,124

[22] Filed: Nov. 12, 1987

[51] Int. Cl.⁴ .............................................. A61N 1/00
[52] U.S. Cl. ................................ 128/786; 128/419 D
[58] Field of Search ............... 128/419 D, 419 P, 786, 128/785, 784

[56] References Cited

U.S. PATENT DOCUMENTS 4,447,239  5/1984  Krütten ........................... 128/419 P
4,699,147  10/1987  Chilson et al. ...................... 128/786

Primary Examiner—Francis Jaworski
Assistant Examiner—George Manuel
Attorney, Agent, or Firm—Limbach, Limbach & Sutton

[57] ABSTRACT

An implantable defibrillation electrode of a shape requiring minimal incision in the body is disclosed. The electrode has a flexible insulated guide and terminates in a preconfigured flexible distal portion with an exposed conductive element. The electrode may be straightened, as for example by insertion of a stylet into the body of the electrode, for ease of insertion into the body.

19 Claims, 2 Drawing Sheets

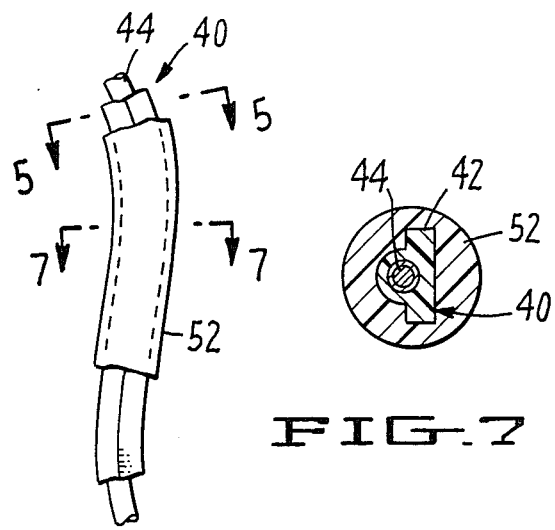
FIG-7
FIG-8
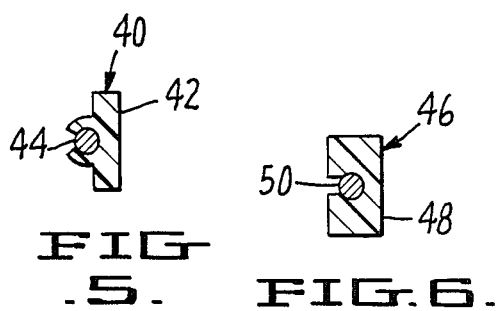
FIG-5.  FIG-6.
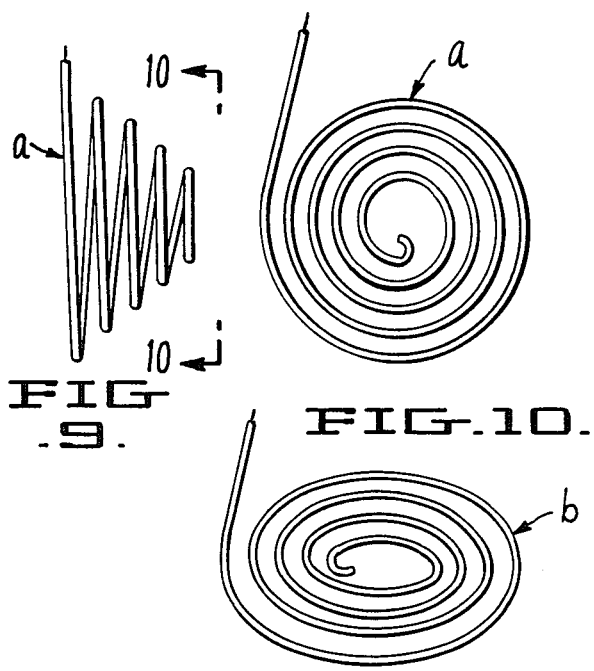
FIG-9.
FIG-10.
FIG-11.
FIG-12.

IMPLANTABLE DEFIBRILLATION ELECTRODE

BACKGROUND OF THE INVENTION

1. Field of the Invention

This invention relates generally to the field of implantable automatic defibrillators, and relates more particularly to electrodes that may be used with such defibrillators.

It is well known in the field of cardiology that certain types of cardiac arrhythmias known as ventricular tachycardia and fibrillation can be effectively treated by the application of electrical shocks to the heart to defibrillate the fibrillating tissues. Such defibrillation may be achieved by the application by medical personnel of electrical paddles to the chest of the patient or directly to the heart tissue, if the chest is open during surgery.

More recent improvements have led to the development of implantable defibrillators which automatically monitor the heart for arrhythmia and initiate defibrillation when arrhythmia occurs. Such devices typically incorporate electrodes which are located either next to the heart or on an intravascular catheter, or both. Because the electrodes are closer to the heart tissue, implanted defibrillators require less electrical energy to stimulate the heart than external electrodes.

However, major surgery is generally necessary to implant present defibrillator lead systems, such as a median sternotomy or lateral thoracotomy. These procedures can be very traumatic to the patient, and may have adverse side effects such as surgical complications, morbidity or mortality. Because of these risks, only those persons whose condition is so dire that the potential benefits outweight the risks are suitable candidates for such surgery, thus excluding many patients who might otherwise benefit from the surgery.

2. Description of the Relevant Art

There have been various attempts to solve these problems, such as that of Heilman, U.S. Pat. No. 4,291,707, and Heilman, U.S. Pat. No. 4,270,549, which respectively show an electrode and the method of implanting it. Heilman teaches the use of rectangular paddle electrodes measuring 4 cm. by 6 cm. Two such electrodes are used, requiring two incisions, one in the abdominal wall and one in the interior thoracic region. Alternatively, one paddle electrode may be inserted through an incision and another intravasculr electrode inserted into the superior vena cava. This still requires two separate intrusions into the body, however.

Another attempted solution involves the use of bipolar electrodes, i.e. a single assembly that contains both electrodes, so that only that single assembly need be put in contact with the heart tissue. Such electrodes are shown in Ackerman, U.S. Pat. No. Re. 27,569, and Alferness, U.S. Pat. No. 4,355,642. However, it is believed that better results are obtained by locating the electrodes on opposite sides of the heart, either side to side or front to back.

Other types of electrodes, some of which may be used transvenously, are shown in Williamson, U.S. Pat. No. 3,749,101, Kallok et al., U.S. Pat. No. 4,355,646, and Moore, U.S. Pat. No. 4,567,900.

It is believed that none of these devices meet the need for an implantable electrode that may be inserted with minimal trauma to the patient while providing adequate surface area for defibrillation.

SUMMARY OF THE INVENTION

In accordance with the illustrated preferred embodiment, the present invention provides for an implantable defibrillator electrode, comprising a flexible insulated guide terminating in a flexible distal portion which includes a conductive element and is of a predetermined configuration, such that it may be extended to a linear configuration by the application of a concentric or axial force and upon the termination of such force assumes said predetermined configuration.

The flexibility of the electrode allows it to be straightened by means of a stylet inserted into the electrode body, and it can then be inserted into the body through a relatively small incision, as for example by the method described in the co-pending application of some applicants entitled Method and Apparatus for Implanting Automatic Implantable Defibrillator, Ser. No. 120,590, filed Nov. 13, 1987. Other techniques for implantation might also be used. The incision required is substantially smaller than that required for a paddle style electrode, thus decreasing the trauma and complications suffered by the patient and allowing more patients to benefit from the procedure.

Once the electrode is inside the body, the stylet may be removed, allowing the distal end of the electrode to assume its preconfigured shape. The shape of the electrode is generally some type of spiral, since this increases the area covered by the electrode and allows it to simulate the function of a paddle style electrode.

The conductive portion of the electrode may be a spiral of wire or of metal foil mounted on a generally cylindrical, non-conductive stem, or one or more wire or metal elements contained in the stem and exposed in a channel on one side of the stem or a series of short cylindrical sections.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

FIG. 5 is a cross-sectional view of another type of electrode constructed according to the present invention.

FIG. 6 is a cross-sectional view of another type of electrode constructed according to the present invention.

FIG. 7 is a cross-sectonal view, taken on the plane designated by line 7—7 of FIG. 8, of the electrode of FIG. 5 inside a catheter.

FIG. 8 is a side view of a portion of the electrode and catheter of FIG. 7.

FIG. 9 is a side view of an electrode showing one configuration that may be used with the present invention.

FIG. 10 is a top view of the electrode of FIG. 9 taken along the plane designated by line 10—10 of FIG. 9.

FIG. 11 is an elevational view of an electrode showing another configuration that may be used with the present invention.

FIG. 12 is a top view of an electrode showing another configuration that may be used with the present invention.

DETAILED DESCRIPTION OF THE PREFERRED EMBODIMENTS

FIGS. 1 through 6 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
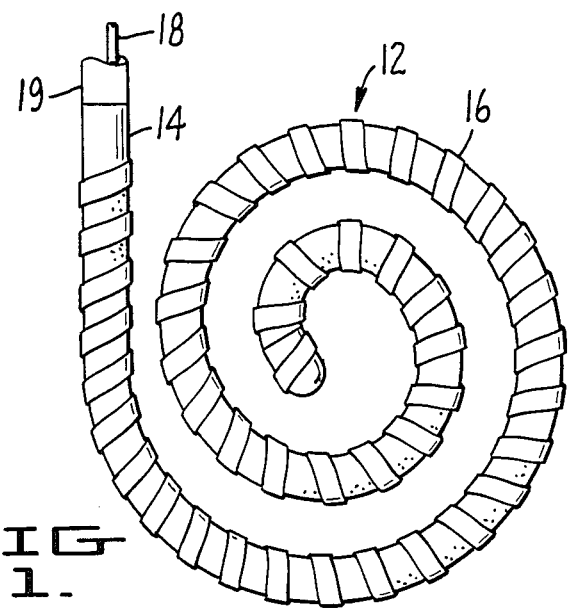
FIG. 1 is a plan view of an electrode constructed according to the present invention.

One embodiment of the present invention is shown in FIG. 1. An electrode 12 has a flexible insulating portion 14, around which is wound a helix of conducting material 16. This conductive material 16 may be metal or foil, and may be of any conductive material, although materials with more structural strength such as titanium or stainless steel are preferred. The helical shape allows for strain relief at the interface between the insulating material 14 and the conductive material 16 when the electrode 12 is bent into its desired configuration. The flexible insulating portion 14 may be made of any biocompatible polymer such as silicone or polyurethane, the latter being favorable as a result of its stiffness and ability to retain the preconfigured shape, as well as the fact that it is chemically inert. The conductive material 16 is connected to the power supply by an internal conductor 18. The proximal end of the electrode 12 is sealed with a connecting pin 19, similar to those commonly found in conventional pacemakers.

Here the electrode 12 has been given a spiral shape, to increase the surface area that comes in contact with the heart tissue and thus simulate the function of a much larger paddle type electrode. However, since the insulating portion 14 is flexible, the electrode may be straightened, for example by inserting a stylet into a center channel, so that the electrode may be inserted through the smallest incision, one barely larger than the diameter of the electrode itself.

Figure 2:
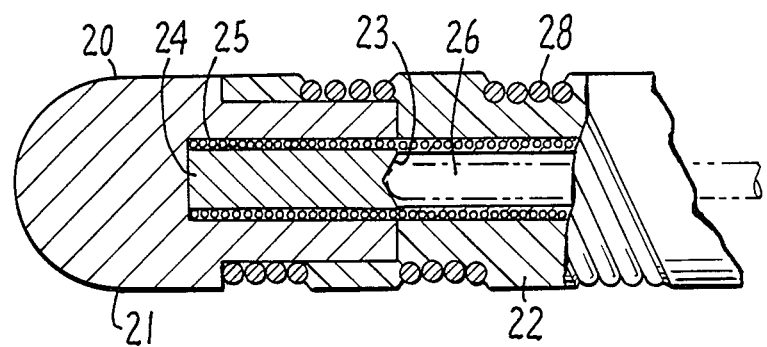
FIG. 2 is a sectional view of another type of electrode constructed according to the present invention.

FIG. 2 shows a variation of this internal construction. The electrode 20 has a metal tip 21 at the end of a flexible insulating portion 22, and has contained within it a center channel 23. At the distal end of the center channel 23 is a metal plug 24. Wound around the interior surface of the center channel 23 is core wire 25. A stylet 26 has been inserted into center channel 24 to straighten out electrode 20 to allow easier insertion into the body. Instead of the flat conductive material 16 of FIG. 1, the outside of electrode 20 is wound with a four strand "quadrafiler" wire 28, which is welded to metal tip 21 and thus connected to the power supply through metal tip 21 and core wire 25. This outside wire 28 is smoother than the flat conductive material 16 of FIG. 1, and should result in less abrasion to the cardiac tissue while providing the same or greater metal surface area to the heart. The wires 25 and 28, the metal tip 21 and metal plug 24 may again be of any conductive material, although titanium seems to be the preferred material for metal tip 21, metal plug 24 and outside wire 28. Core wire 25 is preferably a straight drawn brazed strand wire.

It should be noted that it is not necessary that there by any space between the successive windings of conductive material on the electrodes shown in FIGS. 1 and 2. Standard spring guidewires of the type presently used in radiologic catheterization in vascular and urologic systems, which have contiguous windings, may be used to form the electrodes of the present invention by preconfiguring them as described herein and covering the proximal ends with silicone rubber or similar material, leaving the distal ends exposed for use as electrodes.

Figure 3:
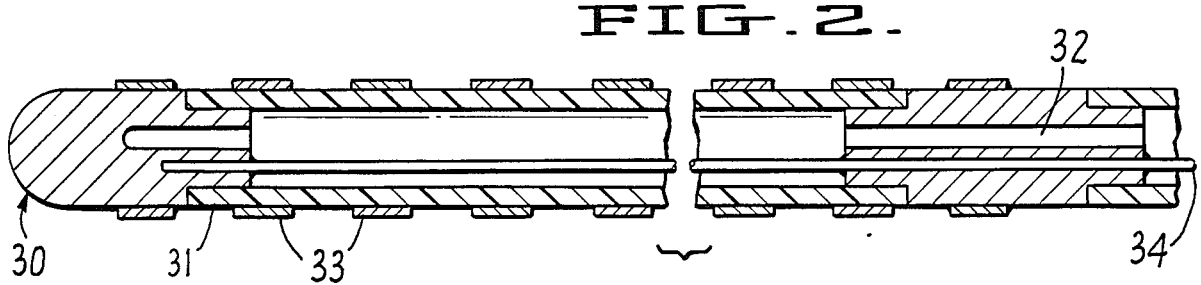
FIG. 3 is a sectional view of another type of electrode constructed according to the present invention.

A different type of construction is shown in FIG. 3. Here an electrode 30 is again composed of a flexible insulating portion 31, and has within it a center channel 32 which may be used for a straightening stylet as described above. However, the conductive element to be in contact with the heart is now not a spiral, but a series of rings of conductive material 33, which are electrically connected within the electrode 30 by a wire 34 which leads to the power supply. Again, the conductive rings 33 may be of any conductive material.

Figure 4:
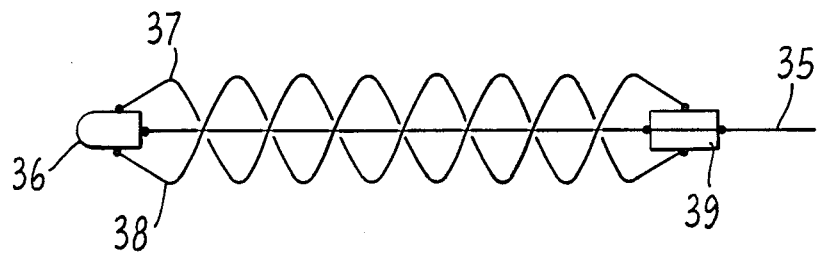
FIG. 4 is a schematic view of another type of electrode constructed according to the present invention, taken on the plane designated by line 5—5 of FIG. 8.

FIG. 4 is a schematic representation of a variation on the embodiments of FIGS. 1 and 2. Instead of a single helix of conductive material, a double helix may be used. Here a center wire 35 runs through the electrode to metal tip 36. Conductive elements 37 and 38 are connected electrically to wire 35 through metal tip 36 and junction 39, and form a double helix on the outside of the electrode. This results in decreasing the electrical resistance of the electrode itself, since the two helical elements will now act as two resistors in parallel, with a resulting resistance of one half the resistance of either alone (assuming two identical helical elements).

Variations of yet another embodiment are shown in FIGS. 5 and 6. FIG. 15 is a cross-sectional view of an electrode 40 which is comprised of a flexible insulating portion 42 with a channel on one side in which is placed a conducting wire 44. Similarly, in FIG. 6, electrode 46 has a flexible insulating portion 48 with a channel holding a conducting wire 50. These electrodes 40 and 46 have the advantage that when they are configured in a spiral shape, the conducting wire 44 or 50 will be exposed on only one side of the plane defined by the spiral, unlike the electrodes described above, which will expose the helical conductive elements on both sides of the spiral. This is designed to limit the application of energy to the direction of the heart and prevent it from being dissipated into the surrounding tissues. In addition, the conductive wire 44 or 50 is removed slightly from the heart surface, eliminating direct myocardial contact by bare metal. Further, in the event of fibrosis around the electrode, the required replacement of the conductive wire 44 or 50 might be accomplished without removing the insulating portion 42 or 48 by merely pulling on the end of the wire 44 or 50 and thus sliding it out of the end of the flexible portion 42 or 48, and then sliding a new wire in. However, the electrodes 40 and 46 have the disadvantage that there is no center channel in which to insert a stylet to straighten them out for insertion into the body.

One way to straighten out this type of electrode without a center channel is shown in FIG. 7. Here the electrode 40 of FIG. 5 is shown inside a catheter 52 which is more rigid than the electrode 40 and which has a channel designed to accept electrode 40. By the application of axial force, the electrode 40 can be straightened and forced into the catheter 52 where the rigidity of the catheter 52 will keep the electrode 40 straight while the entire assembly is inserted into the body. FIG. 8 is a side view of this arrangement. As seen by the lines 5—5 and 7—7 in FIG. 8, the electrode 40 of FIG. 5, containing insulating portion 42 and wire 44, is straightened inside a more rigid catheter 52. Once the proper location is reached, the catheter 52 can be withdrawn over the electrode 40, leaving the electrode 40 in place and allowing it to assume its preconfiguration. Techniques of this type are shown in the co-pending application referred to above.

The electrodes may be of various shapes, as shown in FIGS. 9 through 12 and designated by the letters "a", "b" and "c". These shapes may be applied to any of the aforedescribed electrode constructions. In the preferred embodiment, the electrode is preconfigured as a spiral in order to increase the contact area and thus simulate the function of a paddle electrode. In FIG. 9 the spiral shape a is a conical one which does not lie in a single plane but spirals upward as it spirals inward. FIG. 10 is a top view of this electrode, taken along line 10—10 in FIG. 9. This three-dimensional coil gives the electrode a spring effect between the heart surface and the pericardium which tends to keep the electrode in place.

Alternatively, a flat spiral shape may be used for the electrode. In FIG. 11 a flat round spiral shape "b" for the electrode is shown. In FIG. 12, an electrode having a "square spiral" shape "c" is shown.

The flexible insulating portions of electrodes constructed pursuant to the present invention are typically approximately ⅛ of an inch in diameter. The entire electrode assembly may be as long as 24 inches, of which approximately 18 inches is used as a lead wire, leaving a portion of approximately 6 inches for the preconfigured portion of the electrode which will contact the heart. Whan properly shaped, this portion will produce a spiral that is approximately 2 to 3 inches in diameter.

From the above description, it will be apparent that the invention disclosed herein provides a novel and advantageous electrode for use with implantable defibrillators. The foregoing discussion discloses and describes merely exemplary methods and embodiments of the present invention. As will be understood by those familiar with the art, the invention may be embodied in other specific forms without departing from the spirit or essential characteristics thereof. For example, various other shapes of internal constructions may be used for the electrodes. Accordingly, the disclosure of the present invention is intended to be illustrative, but not limiting, of the scope of the invention, which is set forth in the following claims.

What is claimed is:

1. An implantable defibrillator electrode, comprising:
   a linear guide of a predetermined elongate non-rectilinear configuration, said guide being resiliently deflectable from the non-rectilinear configuration to a generally rectilinear configuration and having an electrically non-conductive exterior surface and a distal portion;
   an electrically conductive element carried by and extending over at least part of the length of said guide, at least a portion of said element being on the exterior surface of the guide;
   guide extension means operatively associated with the guide to selectively:
   (a) deflect the guide into a generally rectilinear configuration; and
   (b) relax the guide for return to the predetermined non-rectilinear configuration.

2. An implantable defibrillator electrode according to claim 1 wherein the guide extension means comprises a hollow channel in the guide and a rigid stylet insertable in said channel.

3. An implantable defibrillator electrode according to claim 1 wherein the guide extension means comprises a catheter of a generally rectilinear configuration having a hollow channel extending therethrough proportioned for snug slidable receipt of the guide.

4. An implantable defibrillator electrode according to claim 1 wherein said conductive element is in the form of a helix which winds around and is attached to the exterior surface of the guide.

5. An implantable defibrillator electrode according to claim 4 wherein the conductive element is comprised of metal foil which is wound around the exterior surface of the distal portion of the guide.

6. An implantable defibrillator electrode according to claim 4 wherein:
   (a) a helical groove is formed in the surface of the distal portion of the flexible insulated guide; and,
   (b) the conductive element is comprised of a wire received in the groove.

7. An implantable defibrillator electrode according to claim 6 wherein the wire is comprised of a plurality of filaments which lie parallel to one another in a single plane and the outer surface of the wire is flush with the outer surface of the guide.

8. An implantable defibrillator electrode according to claim 1 wherein the conductive element is in the form of a double helix which winds around and is attached to the distal portion of the guide.

9. An implantable defibrillator electrode according to claim 1 wherein: the guide is fabricated of an electrically non-conductive material; and the conductive element is received in a channel in the guide and one side of said channel is open and exposes the element to the exterior of the guide.

10. An implantable defibrillator electrode according to claim 1 in which the predetermined configuration is that of a spiral.

11. An implantable defibrillator electrode according to claim 1 in which the predetermined configuration is that of a square spiral.

12. An implantable defibrillator electrode according to claim 10 wherein the spiral configuration of the electrode extends into three dimensions so as not to lie entirely in one plane.

13. An implantable defibrillator electrode according to claim 12 in which the three dimensional spiral of the electrode forms a conical shape.

14. An implantable defibrillator electrode, comprising:
   a linear guide of a predetermined elongate non-rectilinear configuration, said guide being electrically insulative and resiliently deflectable from the non-rectilinear configuration to a generally rectilinear configuration;
   a conductive element carried by and extending through the interior of at least part of the length of said guide;

means for selectively exposing portions of the conductive element to the exterior of the guide comprising a channel along one side of the guide which exposes the conductive element to the exterior of the guide on only said side.

15. An implantable defibrillator electrode, comprising:
   a linear guide of a predetermined elongate non-rectilinear configuration, said guide being electrically insulative and resiliently deflectable from the non-rectilinear configuration to a generally rectilinear configuration;
   a conductive element carried by and extending through the interior of at least part of the length of said guide;
   means for selectively exposing portions of the conductive element to the exterior of the guide;
   guide extension means incorporated in the guide to selectively:
   (a) deflect the guide into a generally rectilinear configuration; and
   (b) relax the guide for return to the predetermined non-rectilinear configuration.

16. An implantable defibrillator electrode according to claim 15 wherein the guide extension means comprises a catheter of a generally rectilinear configuration having a hollow channel extending therethrough proportioned for snug slidable receipt of the guide.

17. A method of constructing an implantable defibrillator electrode, comprising the steps of:
   providing an elongate resilient guide formed into a spiral capable of being resiliently stretched into a generally rectilinear configuration;
   providing said guide with an electrode secured thereto and extending over at least a portion of the length thereof, said electrode being internally electrically insulated by the guide and exposed externally of the guide; and,
   providing means to selectively stretch the guide to a generally rectilinear configuration.

18. The method of claim 17, wherein the means to selectively stretch the guide is provided by extending a channel through the guide and providing a stylet insertable into the channel.

19. The method of claim 17, wherein the means to selectively stretch the guide is provided by a catheter having extending a hollow channel therethrough proportioned for snug slidable receipt of the guide .

* * * * *